United States Patent
Kim et al.

(10) Patent No.: US 10,760,950 B2
(45) Date of Patent: Sep. 1, 2020

(54) APPARATUS AND METHOD FOR PROCESSING ULTRASONIC DATA

(71) Applicant: Samsung Electronics Co., Ltd., Suwon-si (KR)

(72) Inventors: Min Soo Kim, Yongin-si (KR); Do Hyung Kim, Hwaseong-si (KR); Chang Yong Son, Gunpo-si (KR); Kang Eun Lee, Hwaseong-si (KR); Shi Hwa Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 994 days.

(21) Appl. No.: 14/168,626

(22) Filed: Jan. 30, 2014

(65) Prior Publication Data

US 2014/0350892 A1 Nov. 27, 2014

(30) Foreign Application Priority Data

May 24, 2013 (KR) .................... 10-2013-0058888

(51) Int. Cl.
*G01H 17/00* (2006.01)
*A61B 8/08* (2006.01)
*A61B 8/00* (2006.01)

(52) U.S. Cl.
CPC ............ *G01H 17/00* (2013.01); *A61B 8/5207* (2013.01); *A61B 8/5292* (2013.01); *A61B 8/565* (2013.01)

(58) Field of Classification Search
CPC .......... G01H 17/00; G06F 13/14; G06F 13/38
USPC ......................................................... 702/189
See application file for complete search history.

(56) References Cited

U.S. PATENT DOCUMENTS

| | | | | |
|---|---|---|---|---|
| 6,142,946 A * | 11/2000 | Hwang | ..................... | A61B 8/00 600/459 |
| 6,594,315 B1 * | 7/2003 | Schultz | ................... | H03M 7/40 348/E5.108 |
| 8,317,706 B2 * | 11/2012 | Wegener | .................. | A61B 8/06 600/437 |
| 9,042,462 B2 * | 5/2015 | Hanson | ................ | H04B 14/066 341/143 |
| 9,367,445 B2 * | 6/2016 | Lee | .......................... | G06F 3/061 |

(Continued)

FOREIGN PATENT DOCUMENTS

| | | |
|---|---|---|
| JP | 2006-236239 A | 9/2006 |
| JP | 2012-179100 A | 9/2012 |

(Continued)

OTHER PUBLICATIONS

Korean Office Action in counterpart Korean Application No. 10-2013-005888 (2 pages, English translation I); dated Feb. 8, 2018.*

(Continued)

*Primary Examiner* — Hovhannes Baghdasaryan
*Assistant Examiner* — Amie M Ndure
(74) *Attorney, Agent, or Firm* — Sughrue Mion, PLLC

(57) ABSTRACT

An apparatus for processing data including a data compressor configured to compress ultrasonic data, and store the compressed ultrasonic data in a memory; and a data decompressor configured to read the stored ultrasonic data from the memory, decompress the read ultrasonic data, and transfer the decompressed ultrasonic data to a processor configured to perform beamforming.

10 Claims, 6 Drawing Sheets

(56) References Cited

U.S. PATENT DOCUMENTS

| | | | | |
|---|---|---|---|---|
| 2006/0125653 | A1* | 6/2006 | McQuade | B65B 11/02 340/870.07 |
| 2006/0184696 | A1* | 8/2006 | Fallon | G06F 3/0608 709/247 |
| 2006/0190517 | A1* | 8/2006 | Guerrero | G06F 7/762 708/514 |
| 2006/0190644 | A1* | 8/2006 | Fallon | G06F 3/0613 710/68 |
| 2006/0195601 | A1* | 8/2006 | Fallon | G06F 3/0608 709/231 |
| 2006/0206668 | A1* | 9/2006 | Uwatoko | G06F 12/0802 711/118 |
| 2006/0215567 | A1* | 9/2006 | Raghunath | H04L 41/12 370/241 |
| 2006/0221978 | A1* | 10/2006 | Venkatachalam | H04L 47/524 370/395.41 |
| 2006/0256854 | A1* | 11/2006 | Jiang | H04N 19/176 375/240.03 |
| 2007/0016033 | A1* | 1/2007 | Hyun | G01S 15/8906 600/437 |
| 2007/0043939 | A1* | 2/2007 | Fallon | G06F 3/0613 713/2 |
| 2007/0083113 | A1 | 4/2007 | Varghese et al. | |
| 2007/0083746 | A1* | 4/2007 | Fallon | G06F 3/0613 713/1 |
| 2008/0256271 | A1* | 10/2008 | Breed | G06F 12/06 710/52 |
| 2009/0135265 | A1* | 5/2009 | Kawamura | H04N 5/232 348/220.1 |
| 2010/0305449 | A1* | 12/2010 | Wegener | A61B 8/483 600/459 |
| 2010/0331689 | A1* | 12/2010 | Wegener | A61B 8/06 600/443 |
| 2011/0099295 | A1* | 4/2011 | Wegener | H03M 7/46 709/247 |
| 2011/0222791 | A1* | 9/2011 | Mansour | G01S 7/52034 382/240 |
| 2012/0035479 | A1* | 2/2012 | Lim | A61B 8/5207 600/443 |
| 2012/0220877 | A1* | 8/2012 | Takeshima | G01S 7/52034 600/454 |
| 2014/0031695 | A1* | 1/2014 | Lim | A61B 8/5207 600/459 |

FOREIGN PATENT DOCUMENTS

| | | |
|---|---|---|
| KR | 2003-0055430 A | 7/2003 |
| KR | 10-2006-0131686 A | 12/2006 |
| KR | 10-2012-0014522 A | 2/2012 |
| KR | 10-2012-0037918 A | 4/2012 |

OTHER PUBLICATIONS

Korean Office Action, in counterpart Korean Application No. 10-2013-005888 (11 pages, English translation II); dated Feb. 8, 2018.*

Shamdasani, Vijay, Noninvasive ultrasound elastography of atherosclerotic vascular disease: Methods and clinical evaluation, University of Washington, ProQuest Dissertations Publishing, 2008. 3303296. (Year: 2008).*

Korean Office Action dated Feb. 8, 2018, in counterpart Korean Application No. 10-2013-005888 (5 pages, in Korean, no English translation).

Korean Office Action dated Aug. 23, 2018 in corresponding Korean Patent Application No. 10-2003-0058888 (7 pages in English and 5 pages in Korean).

* cited by examiner

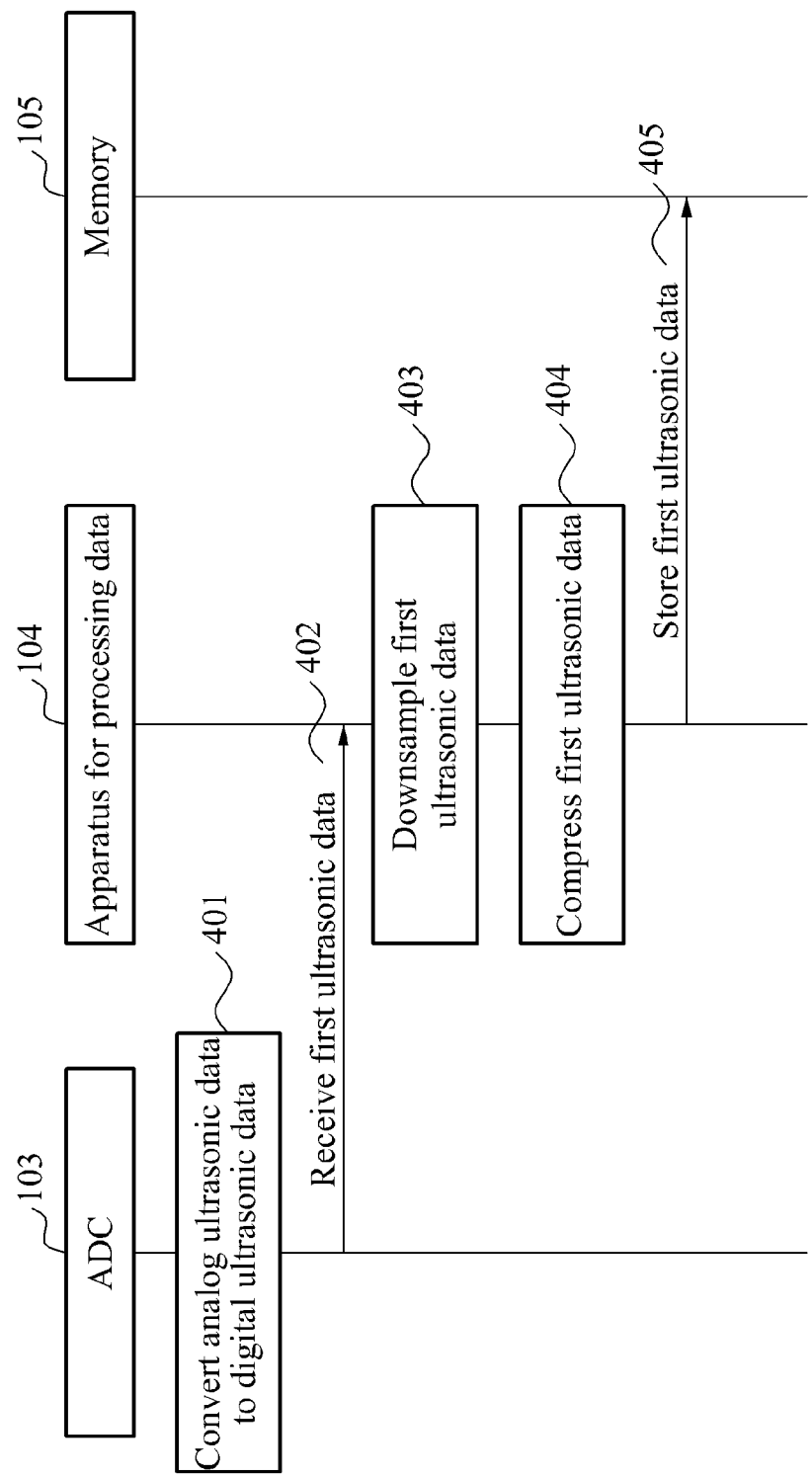

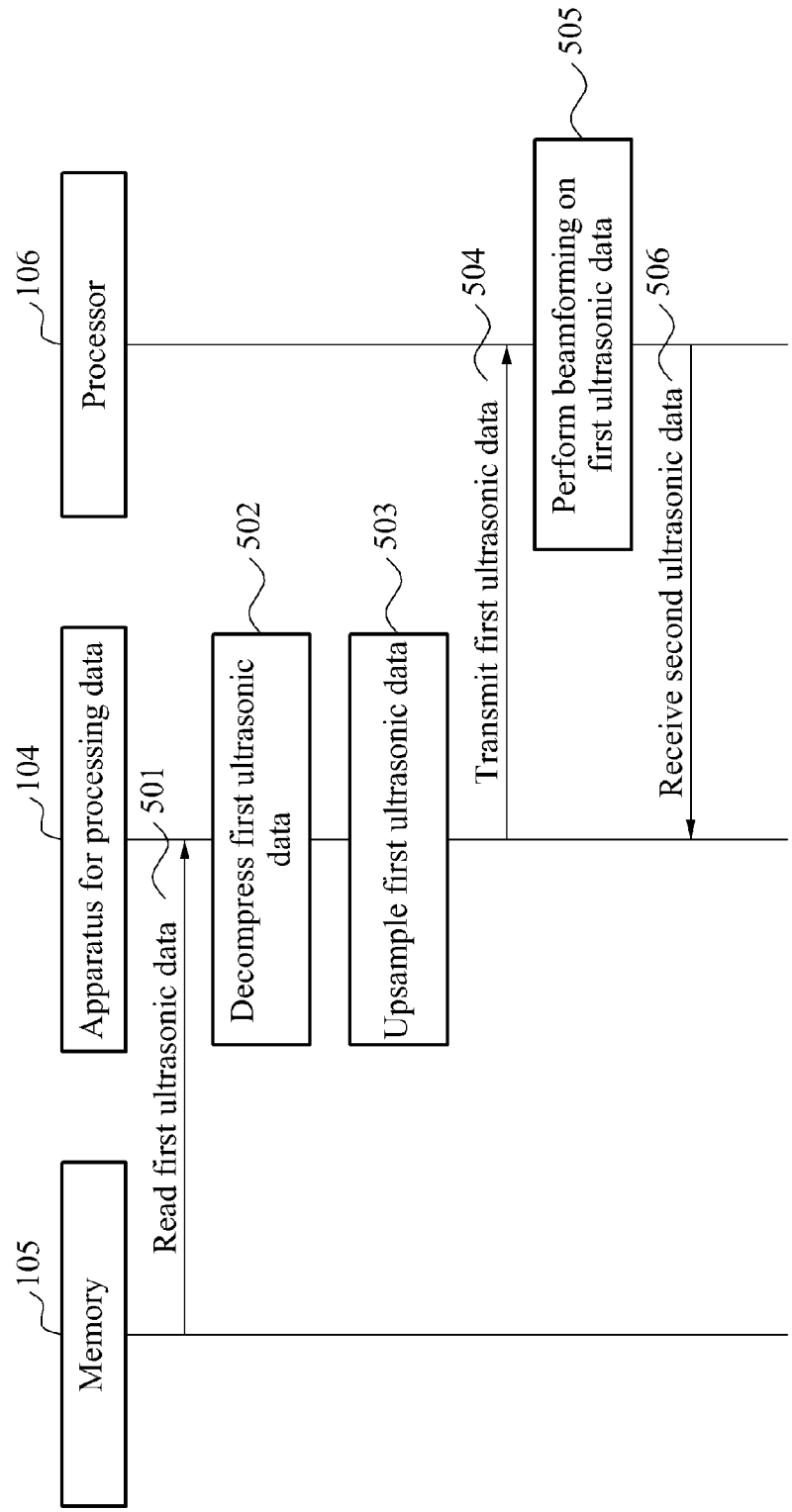

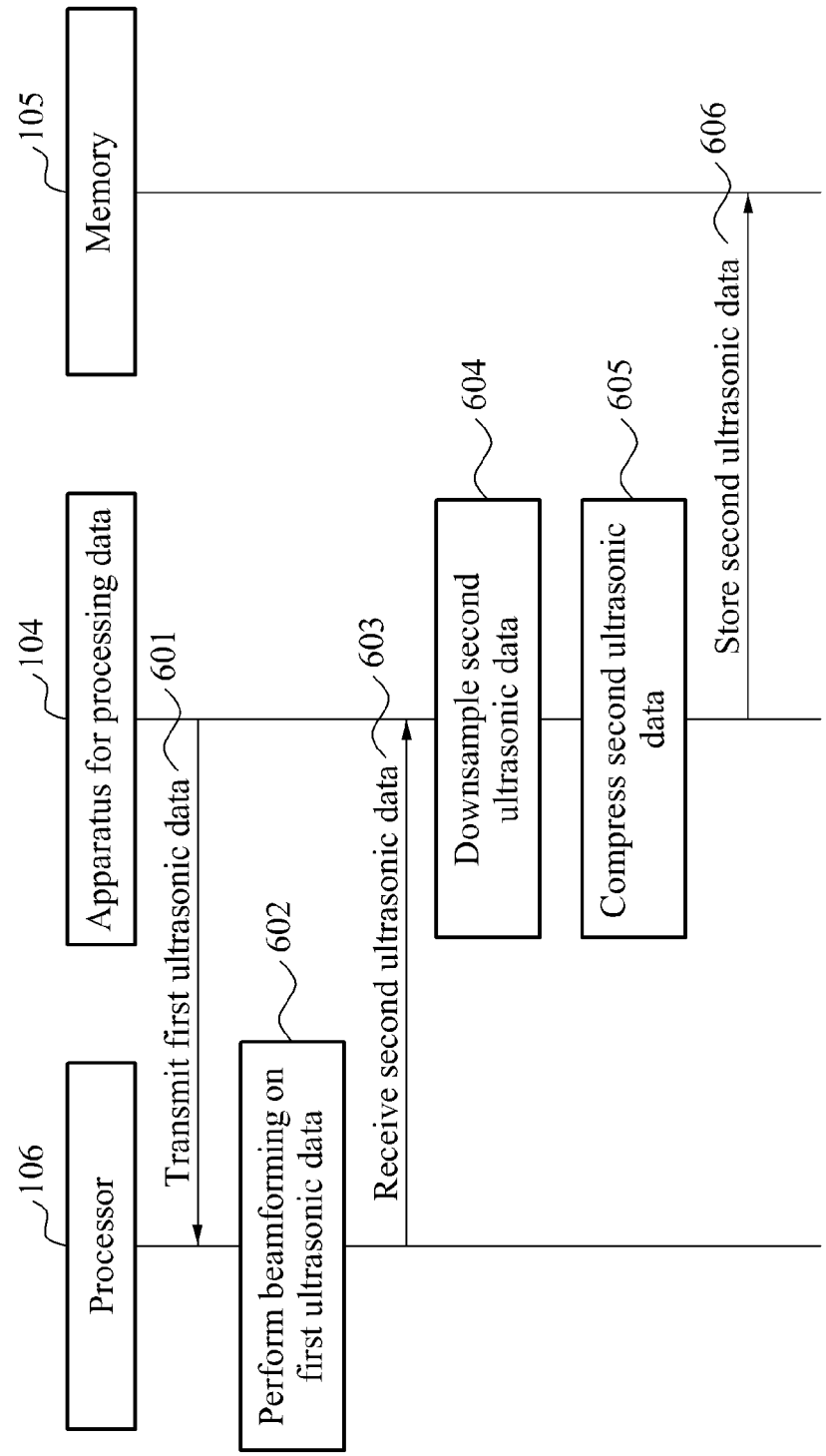

APPARATUS AND METHOD FOR PROCESSING ULTRASONIC DATA

CROSS-REFERENCE TO RELATED APPLICATIONS

This application claims the benefit under 35 USC 119(a) of Korean Patent Application No. 10-2013-0058888 filed on May 24, 2013, in the Korean Intellectual Property Office, the entire disclosure of which is incorporated herein by reference for all purposes.

BACKGROUND

1. Field

The following description relates to an apparatus and method for processing data that compresses ultrasonic data and stores the compressed ultrasonic data.

2. Description of Related Art

When beamforming is performed on multiple channel data in an ultrasonic diagnostic apparatus, mass storage ultrasonic data may be generated. When a computing device, for example, a processor, accesses such ultrasonic data and performs beamforming on the ultrasonic data, a large scale storage device may be necessary. Also, a large memory operation cycle may be needed to read/write mass storage data.

Also, in general, an additional process of upscaling may be needed because sampled ultrasonic data may be stored for use in performing, thereby increasing a computing load of the processor.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for processing data includes a data compressor configured to compress first ultrasonic data, and store the compressed first ultrasonic data in a memory; and a data decompressor configured to read the stored first ultrasonic data from the memory, decompress the read first ultrasonic data, and transfer the decompressed first ultrasonic data to a processor configured to perform beamforming.

The data compressor may be further configured to receive second ultrasonic data obtained as a result of the beamforming from the processor, compress the received second ultrasonic data, and store the compressed second ultrasonic data in the memory.

The data decompressor may be further configured to read the stored second ultrasonic data from the memory, and decompress the read second ultrasonic data.

The apparatus may be configured to receive control information from the processor, and determine whether to enable the data compressor and the data decompressor to perform the compressing and the decompressing based on the received control information.

The data compressor may include a data downsampler configured to downsample the first ultrasonic data; and the data compressor may be further configured to compress the downsampled first ultrasonic data, and store the compressed downsampled first ultrasonic data in the memory.

The data decompressor may include a data upsampler configured to upsample the decompressed first ultrasonic data; and the data decompressor may be further configured to transfer the upsampled first ultrasonic data to the processor.

In another general aspect, an apparatus for processing data includes a data downsampler configured to downsample first ultrasonic data; a data compressor configured to compress the downsampled first ultrasonic data, and store the compressed first ultrasonic data in a memory; a data decompressor configured to read the compressed first ultrasonic data from the memory, and decompress the read first ultrasonic data; and a data upsampler configured to upsample the decompressed first ultrasonic data; and the data decompressor may be further configured to transfer the upsampled first ultrasonic data to a processor configured to perform beamforming.

The apparatus may further include an internal cache; and the data compressor may be further configured to temporarily store the upsampled first ultrasonic data in the internal cache.

The apparatus may be configured to receive control information from the processor, and determine whether to enable the data compressor and the data decompressor to perform the compressing and the decompressing based on the received control information.

The data compressor may be further configured to receive second ultrasonic data obtained as a result of the beamforming from the processor, compress the received second ultrasonic data, and store the compressed second ultrasonic data in the memory.

The data decompressor may be further configured to read the stored second ultrasonic data from the memory, and decompress the read second ultrasonic data.

In another general aspect, a method of processing data includes downsampling first ultrasonic data; compressing the downsampled first ultrasonic data; storing the compressed first ultrasonic data in a memory; reading the stored first ultrasonic data from the memory; decompressing the read first ultrasonic memory; upsampling the decompressed first ultrasonic data; and transferring the upsampled first ultrasonic data to a processor configured to perform beamforming.

The method of claim may further include temporarily storing the upsampled first ultrasonic data in an internal cache accessible by a plurality of processors configured to be capable of requesting the first ultrasonic data.

The method may further include receiving control information from the processor; and determining whether to perform the compressing and the decompressing based on the received control information.

The method may further include receiving second ultrasonic data obtained as a result of the beamforming from the processor; compressing the received second ultrasonic data; and storing the compressed second ultrasonic data in the memory.

The method may further include reading the stored second ultrasonic data from the memory; and decompressing the read second ultrasonic data.

In another general aspect, a method of processing data includes reducing an amount of ultrasonic data; storing the reduced amount of ultrasonic data in a memory; reading the stored ultrasonic data from the memory; increasing an amount of the read ultrasonic data; and transferring the increased amount of ultrasonic data to a processor configured to perform beamforming.

The reducing of the amount of the ultrasonic data may include compressing the ultrasonic data; and the increasing of the amount of the read ultrasonic data may include decompressing the read ultrasonic data.

The reducing of the amount of the ultrasonic data may include downsampling the ultrasonic data, and compressing the downsampled ultrasonic data; and the increasing of the amount of the read ultrasonic data may include decompressing the read ultrasonic data, and upsampling the decompressed ultrasonic data.

The method may further include receiving control information from the processor; and determining how to perform the decreasing of the amount of the ultrasonic data and the increasing of the amount of the read ultrasonic data based on the received control information.

Other features and aspects will be apparent from the following detailed description, the drawings, and the claims.

BRIEF DESCRIPTION OF THE DRAWINGS

FIG. 4 illustrates an example of a process of storing original ultrasonic data in a memory.

FIG. 5 illustrates an example of a process of transferring ultrasonic data to a processor.

FIG. 6 illustrates an example of a process of storing ultrasonic data on which beamforming has been performed in a memory.

DETAILED DESCRIPTION

Figure 1:
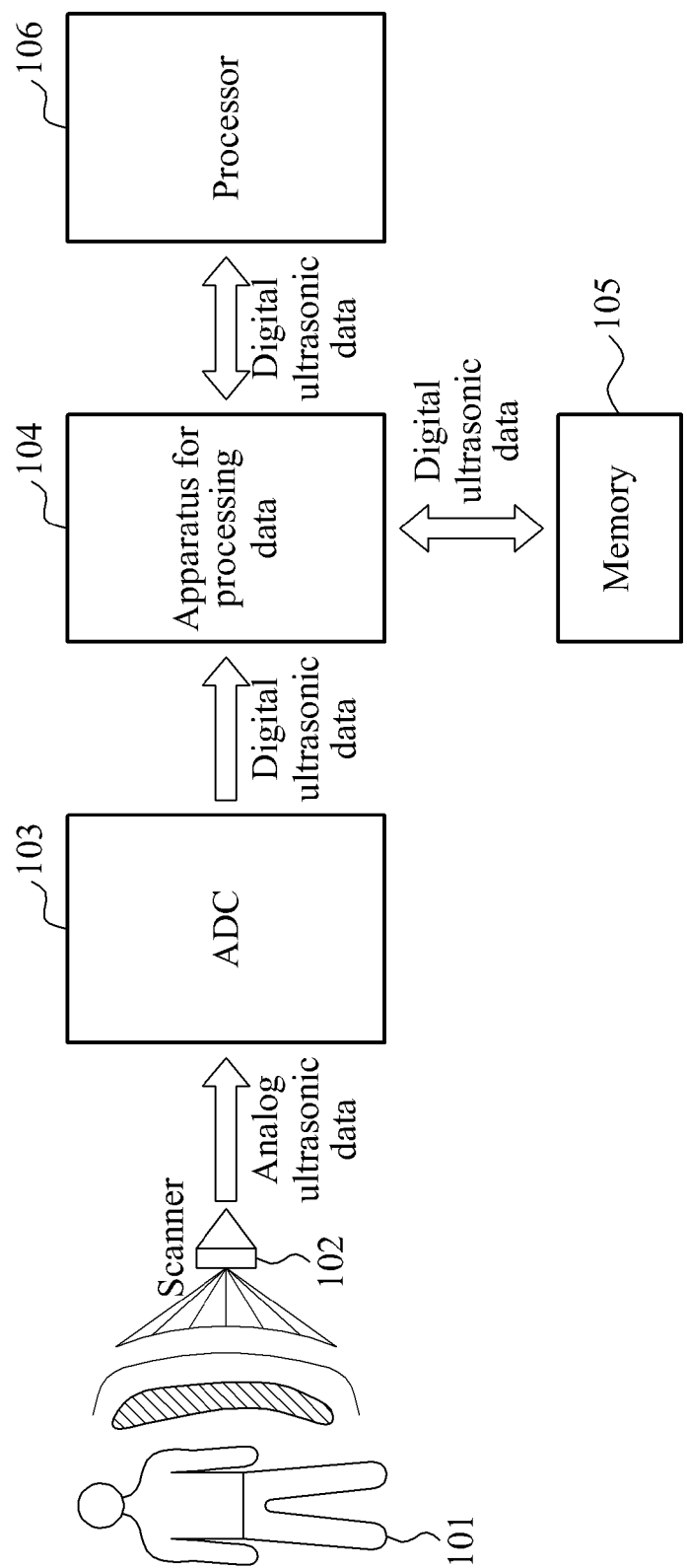
FIG. 1 illustrates an example of an operation of an apparatus for processing data.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

When a computing device, for example, a processor, performs beamforming, an apparatus for processing data may reduce a size of memory needed for the processor, and reduce a memory operation cycle needed for accessing the ultrasonic data stored in the memory. Also, the apparatus for processing the data may perform upscaling needed for the beamforming of the ultrasonic data, and thereby decrease a computing load of the processor when the processor performs the beamforming.

FIG. 1 illustrates an example of an operation of an apparatus 104 for processing data. Referring to FIG. 1, an ultrasonic signal is radiated toward a body 101 from a probe of a scanner 102. The ultrasonic signal radiated toward the body 101 is reflected by an internal tissue boundary of the body 101, and the probe of the scanner 102 converts the reflected ultrasonic signal into analog ultrasonic data.

An analog to digital converter (ADC) 103 converts the analog ultrasonic data into digital ultrasonic data. The apparatus 104 for processing the data stores the digital ultrasonic data in a memory 105.

When a processor 106 performs beamforming, the apparatus 104 for processing the data reads the digital ultrasonic data stored in the memory 105, and transfers the read digital ultrasonic data to the processor 106. The apparatus 104 for processing the data receives the beamformed digital ultrasonic data, and stores the received digital ultrasonic data in the memory 105.

The apparatus 104 for processing the data may include elements for compressing and decompressing ultrasonic data prior to storing the ultrasonic data in the memory to reduce a storage space needed for storing the ultrasonic data, and decrease a memory operation cycle of the memory 105.

Also, the apparatus 104 for processing the data may include an element for performing upscaling when decompressing the ultrasonic data so that the processor 106 does not have to perform the upscaling, thereby reducing an amount of computation the processor 106 needs to perform.

Figure 2:
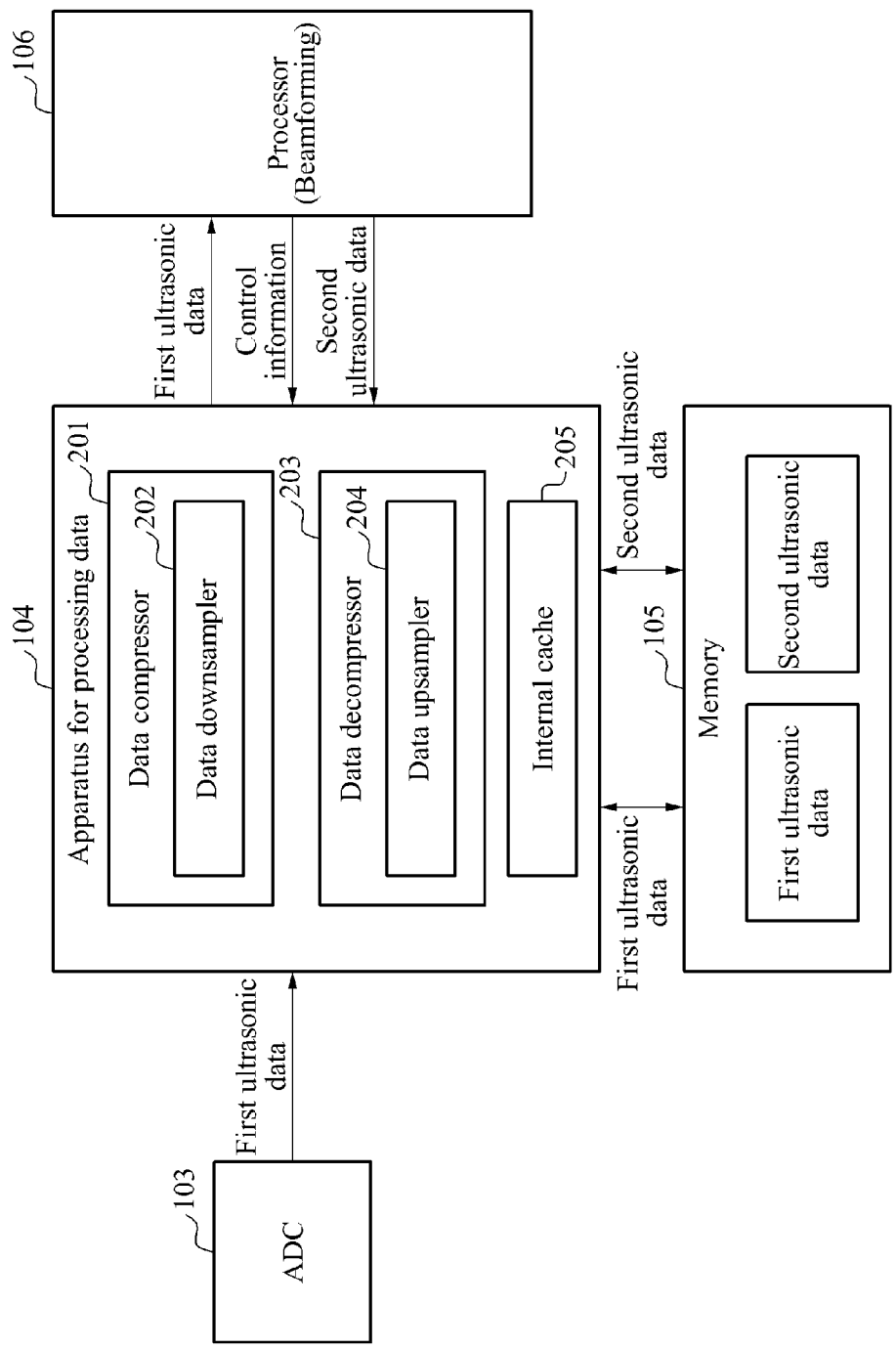
FIG. 2 illustrates an example of a detailed configuration of an apparatus for processing data.

FIG. 2 illustrates an example of a detailed configuration of an apparatus 104 for processing data. Referring to FIG. 2, the apparatus 104 for processing the data includes a data compressor 201, a data decompressor 203, and an internal cache 205. However, the internal cache 205 may be omitted. The data compressor 201 includes a data downsampler 202, and the data decompressor 203 includes a data upsampler 204. However, the data downsampler 202 and the data upsampler 204 may be omitted. The apparatus 104 for processing the data may receive control information from the processor 106, and may determine whether to enable the data compressor 201 and the data decompressor 203 to compress and decompress ultrasonic data based on the received control information, and may determine whether to enable or disable the data downsampler 202 and the data upsampler 204 to downsample and upsample ultrasonic data based on the received control information.

The apparatus 104 for processing the data receives first ultrasonic data from the ADC 103. The first ultrasonic data is original ultrasonic data on which beamforming has not been performed. The data compressor 201 compresses the first ultrasonic data, and stores the compressed first ultrasonic data in the memory 105.

If included or enabled, the data downsampler 202 downsamples the first ultrasonic data, and the data compressor 201 compresses the downsampled first ultrasonic data and stores the compressed downsampled first ultrasonic data in the memory 105.

When the apparatus 104 for processing the data receives a request for the first ultrasonic data from the processor 106, the data decompressor 203 reads the compressed first ultrasonic data from the memory 105. The processor 106 may request first ultrasonic data corresponding to a predetermined address of the memory 105.

The data decompressor 203 decompresses the compressed first ultrasonic data read from the memory 105, and transfers the decompressed first ultrasonic data to the processor 106. If the data downsampler 202 and the data upsampler 204 are included or enabled, the decompressed first ultrasonic data is downsampled first ultrasonic data, so the data upsampler 204 upsamples the decompressed first ultrasonic data, and the data decompressor 203 transfers the upsampled first ultrasonic data to the processor 106.

The processor 106 outputs second ultrasonic data after performing the beamforming on the first ultrasonic data received from the apparatus 104 for processing the data. Thus, the second ultrasonic data is beamformed ultrasonic data. The processor 106 transfers the second ultrasonic data to the apparatus 104 for processing the data.

The data compressor 201 compresses the second ultrasonic data, and stores the compressed second ultrasonic data in the memory 105. When the processor 106 requests the second ultrasonic data stored in the memory 105, the apparatus 104 for processing the data processes the second ultrasonic data the same way the apparatus 104 for processing the data processes the first ultrasonic data as described above.

The aforementioned downsampling, compressing, decompressing, and upsampling of the ultrasonic data may be controlled by the processor 106. Also, as necessary, the apparatus 104 for processing the data may store the first ultrasonic data and the second ultrasonic data in the memory 105 without performing the downsampling, compressing, decompressing, and upsampling of the ultrasonic data. More particularly, the apparatus 104 for processing the data may process the first ultrasonic data or the second ultrasonic data corresponding to a predetermined address needed by the processor 106.

Referring to FIG. 2, the processor 106 may transmit the ultrasonic data to the apparatus 104 for processing the data or receive the ultrasonic data from the apparatus 104 for processing the data without accessing the memory 105 directly. Accordingly, the apparatus 104 for processing the data may reduce an amount of the memory 105 needed for performing the beamforming.

The apparatus 104 for processing the data reduces the amount of the memory 105 needed for performing the beamforming because the apparatus 104 for processing the data compresses the ultrasonic data received from the ADC 103 and stores the compressed ultrasonic data in the memory 105. Also, the apparatus 104 for processing the data reduces the amount of the memory 105 needed to store the beamformed ultrasonic data because the apparatus 104 for processing the data compresses the beamformed ultrasonic data before storing the beamformed ultrasonic data in the memory 105.

Further, when the processor 106 requests the ultrasonic data corresponding to a predetermined address of the memory 105, a computing load of the processor 106 may be reduced because the apparatus 104 for processing the data performs the upsampling needed for a beamforming process of the ultrasonic data.

Figure 3:
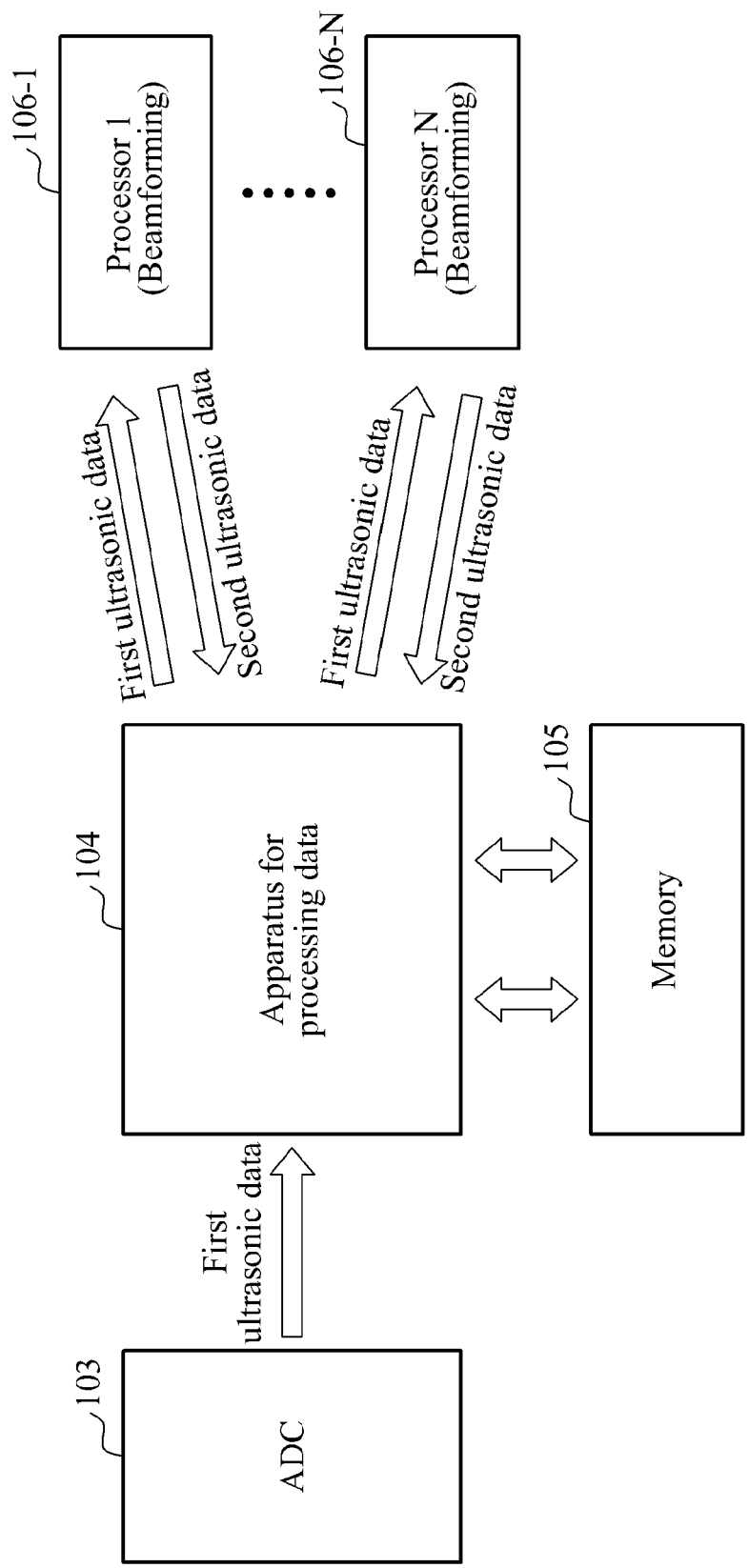
FIG. 3 illustrates an example of an operation of an apparatus for processing data when a plurality of processors perform beamforming.

FIG. 3 illustrates an example of an operation of an apparatus 104 for processing data when a plurality of processors 106-1 through 106-N perform beamforming. In particular, FIG. 3 illustrates an example in which the processor of FIG. 2 corresponds to the plurality of processors 106-1 through 106-N in FIG. 3. Referring to FIG. 3, the apparatus 104 for processing the data receives digital first ultrasonic data from an ADC. The apparatus 104 for processing the data compresses the first ultrasonic data, and stores the compressed first ultrasonic data in the memory 105.

When the apparatus 104 for processing the data receives a request for beamforming of the first ultrasonic data from the plurality of processors 106-1 through 106-N, the apparatus 104 for processing the data decompresses the first ultrasonic data stored in the memory 105, and transfers the decompressed first ultrasonic data to the plurality of processors 106-1 through 106-N. When the first ultrasonic data is downsample before being compressed, the apparatus 104 for processing the data upsamples the decompressed first ultrasonic data.

The apparatus 104 for processing the data may temporarily store the decompressed first ultrasonic data in the internal cache 205 of the apparatus 104 for processing the data shown in FIG. 2, and may transfer the stored first ultrasonic data to the plurality of processors 106-1 to 106-N requesting the first ultrasonic data.

When the first ultrasonic data is downsampled, the apparatus 104 for processing the data may temporarily store the upsampled first ultrasonic data in the internal cache 205. In particular, the apparatus 104 for processing the data may store calculation results in the internal cache 205 to avoid the need to perform the same calculations on the ultrasonic data each time a different one of the plurality of processors 106-1 through 106-N requests the ultrasonic data.

The above description of FIG. 3 refers to the first ultrasonic data, but the same process may be applied to second ultrasonic data obtained as a result of the beamforming performed by the processor 106.

FIG. 4 illustrates an example of a process of storing original ultrasonic data in a memory. In 401, the ADC 103 converts analog ultrasonic data into digital ultrasonic data. In 402, the apparatus 104 for processing the data receives the digital first ultrasonic data from the ADC 103. The first ultrasonic data is original ultrasonic data on which beamforming has not been performed.

In 403, the apparatus 104 for processing the data downsamples the first ultrasonic data. In 404, the apparatus 104 for processing the data compresses the downsampled first ultrasonic data.

In 405, the apparatus 104 for processing the data stores the compressed downsampled first ultrasonic data in the memory 105. However, the operations of 403 and 404 of FIG. 4 may not be necessary. For example, the first ultrasonic data may be compressed and stored in the memory 105 without being downsampled. Also, the first ultrasonic data may be stored in the memory 105 directly without being downsampled and compressed, FIG. 5 illustrates an example of a process of transferring ultrasonic data to a processor. The processor 106 requests the first ultrasonic data stored in the memory 105 to perform beamforming. In 501, the apparatus 104 for processing the data reads the first ultrasonic data requested by the processor 106 from the memory 105. In 502, the apparatus 104 for processing the data decompresses the compressed first ultrasonic data. In 503, the apparatus 104 for processing the data upsamples the decompressed first ultrasonic data.

As described in FIG. 4, the first ultrasonic data may be downsampled and compressed before being stored in the memory 105, or may be compressed and stored in the memory 105 without the downsampling, or may be directly stored in the memory 105 without the downsampling and the compressing.

When the first ultrasonic data is downsampled and compressed, the apparatus 104 for processing the data performs both operations 502 and 503. When the first ultrasonic data is compressed without being downsampled, the apparatus 104 for processing the data performs 502 but does not perform 503. When the first ultrasonic data is stored in the memory 105 without being downsampled and compressed, the apparatus 104 for processing the data does not perform either of 502 or 503.

In 504, the apparatus 104 for processing the data transmits the first ultrasonic data to the processor 106. When the plurality of processors 106 request the same first ultrasonic data, the apparatus 104 for processing the data may temporarily store a result of performing 502 or 503 in the internal cache 205 shown in FIG. 2.

In 505, the processor 106 performs beamforming on the first ultrasonic data received from the apparatus 104 for processing the data. In 506, the apparatus 104 for processing the data receives second ultrasonic data obtained as a result of the beamforming from the processor 106.

FIG. 6 illustrates an example of a process of storing ultrasonic data on which beamforming has been performed in a memory. In 601, the apparatus 104 for processing the data transmits first ultrasonic data to the processor 106. In 602, the processor 106 performs beamforming on the first ultrasonic data received from the apparatus 104 for processing the data. In 603, the apparatus 104 for processing the data second ultrasonic data obtained as a result of the beamforming from the processor 106.

In 604, the apparatus 104 for processing the data downsamples the received second ultrasonic data. In 605, the apparatus 104 for processing the data compresses the downsampled second ultrasonic data. In 606, the apparatus 104 for processing the data stores the compressed downsampled second ultrasonic data in the memory 105.

However, it may not be necessary to perform operations 604 and 605 FIG. 6. In particular, the second ultrasonic data may be compressed and stored in the memory 105 without the downsampling. Also, the second ultrasonic data may be directly stored in the memory 105 without the downsampling and the compressing.

An apparatus for processing data may be an interface between a memory for storing ultrasonic data and a plurality of processors for beamforming the ultrasonic data. The apparatus for processing the data may compress/decompress the ultrasonic data. The apparatus for processing the data may downsample/upsample the ultrasonic data as necessary. Also, the apparatus for processing the data may include an internal cache for temporarily storing a result of upsampling for a plurality of processors requesting the same ultrasonic data. The apparatus for processing the data may determine whether to perform compressing/decompressing and downsampling/upsampling based on control information received from the plurality of processors.

An amount of storage space needed for mass storage of ultrasonic data may be reduced by compressing the ultrasonic data. When data of 256 channels, 256 scan lines, and 16 frames is stored without the compressing, a storage space of approximately 13.4 gigabytes (GB) may be needed, so a mobile device may not store the ultrasonic data without the compressing. However, when the ultrasonic data is compressed by a factor of ⅓ using, for example, a visually lossless algorithm that is randomly accessible, a storage space of only 4.5 GB may be needed, so the ultrasonic data may be stored in the mobile device.

A memory operation cycle of 214 gigahertz (GHz) may be needed when the processor accesses 256 channels, 256 scan lines, and 30 frames per second (fps) of ultrasonic data without compressing the ultrasonic data. In particular, when the ultrasonic data is not compressed, a memory operation cycle needed for accessing the memory may be excessive. However, when the visually lossless algorithm and a memory processing unit (MemPU) accessing the memory in which the ultrasonic data is stored are used, the memory operation cycle may be reduced to 3.2 GHz, for example. The MemPU may be included in a single device through being used along with the apparatus for processing the data. Also, a computing load of the processor may be reduced because the processor does not upsample the ultrasonic data directly.

The apparatus for processing data 104, the data compressor 201, the data downsampler 202, the data decompressor 203, and the data upsampler 204 described above that perform the operations illustrated in FIGS. 1-6 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for processing data, the apparatus comprising:
   a data compressor configured to compress a first ultrasonic data, on which beamforming is not performed, and store the compressed first ultrasonic data in a memory;
   a data decompressor configured to read the stored first ultrasonic data from the memory, decompress the read first ultrasonic data, and transfer the decompressed first ultrasonic data to a processor configured to perform beamforming; and
   an internal cache configured to temporarily store the decompressed first ultrasonic data in the internal cache accessible by a plurality of processors configured to perform beamforming and transfer the decompressed first ultrasonic data from the plurality of processors in response to a request for the decompressed first ultrasonic data from the plurality of processors so that the plurality of processors do not have to perform the decompressing and the upsampling, the internal cache being external to the plurality of processors,
   wherein the data decompressor upsamples the decompressed first ultrasonic data if the stored first ultrasonic data is a compressed and downsampled first ultrasonic data, and transfers the upsampled first ultrasonic data to the processor so that the processor does not have to perform the decompressing and the upsampling, and
   wherein the data compressor is further configured to receive a second ultrasonic data obtained as a result of the beamforming from the processor, compress the received second ultrasonic data, and store the compressed second ultrasonic data in the memory.

2. The apparatus of claim 1, wherein the data decompressor is further configured to read the stored second ultrasonic data from the memory, and decompress
   the read second ultrasonic data.

3. The apparatus of claim 1, wherein the apparatus is configured to receive control information from the processor, and determine whether to enable the data compressor and the data decompressor to perform the compressing and the decompressing based on the received control information.

4. The apparatus of claim 1, wherein the data compressor comprises a data downsampler configured to downsample the first ultrasonic data; and
   the data compressor is further configured to compress the downsampled first ultrasonic data, and store the compressed and downsampled first ultrasonic data in the memory.

5. An apparatus for processing data, the apparatus comprising:
   a data downsampler configured to downsample a first ultrasonic data, on which beamforming is not performed;
   a data compressor configured to compress the downsampled first ultrasonic data, and store the compressed first ultrasonic data in a memory;
   a data decompressor configured to read the compressed first ultrasonic data from the memory, and decompress the read first ultrasonic data;

a data upsampler configured to upsample the decompressed first ultrasonic data if the stored first ultrasonic data is a compressed and downsampled first ultrasonic data; and an internal cache configured to temporarily store the upsampled first ultrasonic data in the internal cache accessible by a plurality of processors configured to perform beamforming and transfer the upsampled first ultrasonic data to the plurality of processors in response to a request for the upsampled first ultrasonic data from plurality of processors so that the plurality of processors do not have to perform the decompressing and the upsampling, the internal cache being external to the plurality of processors, wherein the data decompressor is further configured to transfer the upsampled first ultrasonic data to a processor configured to perform beamforming so that the processor does not have to perform the decompressing and the upsampling, and wherein the data compressor is further configured to receive a second ultrasonic data obtained as a result of the beamforming from the processor, compress the received second ultrasonic data, and store the compressed second ultrasonic data in the memory.

6. The apparatus of claim 5, wherein the apparatus is configured to receive control information from the processor, and determine whether to enable the data compressor and the data decompressor to perform the compressing and the decompressing based on the received control information.

7. The apparatus of claim 5, wherein the data decompressor is further configured to read the stored second ultrasonic data from the memory, and decompress the read second ultrasonic data.

8. A method of processing data, the method comprising:

compressing a first ultrasonic data, on which beamforming is not performed, wherein the compressing of the first ultrasonic data comprises downsampling the first ultrasonic data;

storing the compressed first ultrasonic data in a memory;

reading the stored first ultrasonic data from the memory;

decompressing the read first ultrasonic data, wherein the decompressing of the read first ultrasonic data comprises upsampling the decompressed first ultrasonic data if the read first ultrasonic data is a compressed and downsampled first ultrasonic data;

temporarily storing the upsampled first ultrasonic data in an internal cache accessible by of processors configured to perform beamforming;

transferring the upsampled first ultrasonic data to the plurality of processors in response to a request for the upsampled first ultrasonic data from the plurality of processors so that the plurality of processors do not have to perform the decompressing and the upsampling;

receiving a second ultrasonic data obtained as a result of the beamforming from the processor;

compressing the received second ultrasonic data; and storing the compressed second ultrasonic data in the memory, wherein the internal cache is external to the plurality of processors.

9. The method of claim 8, further comprising:

receiving control information from the processor; and determining whether to perform the compressing and the decompressing based on the received control information.

10. The method of claim 8, further comprising:

reading the stored second ultrasonic data from the memory; and decompressing the read second ultrasonic data.

* * * * *